United States Patent [19]

Angelsen et al.

[11] Patent Number: 4,887,605
[45] Date of Patent: Dec. 19, 1989

[54] LASER CATHETER DELIVERY SYSTEM FOR CONTROLLED ATHEROMA ABLATION COMBINING LASER ANGIOPLASTY AND INTRA-ARTERIAL ULTRASONIC IMAGINING

[76] Inventors: Bjorn A. J. Angelsen, Anders Tvereggens veg 34, 7000 Trondheim; David Linker, Kofoedgeilan 10 A, 7018 Trondheim, both of Norway

[21] Appl. No.: 157,407

[22] Filed: Feb. 18, 1988

[51] Int. Cl.[4] .......................... A61B 8/12; A61B 17/36
[52] U.S. Cl. ............................ 128/660.03; 128/660.07; 128/395; 606/7; 606/18
[58] Field of Search ...................... 128/303.1, 395, 397, 128/398, 4-6, 660.03, 660.05, 660.07, 660.10, 916

[56] References Cited

U.S. PATENT DOCUMENTS

| | | | |
|---|---|---|---|
| 3,918,438 | 11/1975 | Hayamizu et al. | 128/4 |
| 4,313,444 | 2/1982 | Glenn | 128/660.05 |
| 4,445,892 | 5/1984 | Hussein et al. | 128/4 |
| 4,466,444 | 8/1984 | Baba | 128/4 |
| 4,476,874 | 10/1984 | Taenzer et al. | 128/660.05 |
| 4,508,122 | 4/1985 | Gardineer et al. | 128/660.1 |
| 4,558,706 | 12/1985 | Nakada et al. | 128/4 |
| 4,576,177 | 3/1986 | Webster, Jr. | 128/303.1 |
| 4,587,972 | 5/1986 | Morantte, Jr. | 128/303.1 |
| 4,648,892 | 3/1987 | Kittrell et al. | 128/303.1 |
| 4,672,963 | 6/1987 | Barken | 128/303.1 |
| 4,718,406 | 1/1988 | Bregman et al. | 128/6 |
| 4,737,628 | 4/1988 | Lovoi | 128/395 |

Primary Examiner—Lee S. Cohen
Assistant Examiner—David Shay
Attorney, Agent, or Firm—Cohen, Pontani & Lieberman

[57] ABSTRACT

Laser catheter delivery system for controlled ablation of atheroma, combining laser angioplasty and intra-arterial ultrasonic imaging. In laser ablation of atheroma, dosage and directing of the laser light beam represent critical problems, since accurate removal of the atheroma is required without damaging of the arterial wall. The present system comprise a combined laser and ultrasound catheter composed of apparatus for emitting a laser beam in an artery towards an atheroma for ablation of the atheroma an optical fiber assembly for feeding laser light from a laser to the emitting apparatus an ultrasound transducer for intra-arterial imaging of tissue structures like the atheroma, the vessel wall and surrounding tissue, by emitting a pulsed ultrasound beam towards the tissue structures and also arranged to receive backscattered ultrasound from the tissue structures beam directing apparatus arranged to direct the ultrasound beam towards the tissue structures and also arranged so that the laser beam can be brought into for practical purposes any of the directions the ultrasound beam can assume for imaging, so that the laser beam can be steered towards a portion of the ultrasound image indicating a portion of an atheroma to ablate that portion of the atheroma receive circuits adapted to receive and process the backscattered ultrasound for imaging of the tissue structures, and apparatus for analysing the ultrasound image, either manually or automatically, to determine the presence of atheroma so that the image can be used to direct the laser beam towards the regions in the ultrasound image which have been determined to represent a portion of an atheroma and determine the intensity and the dosage of the laser beam for accurate ablation of that portion of the atheroma.

12 Claims, 6 Drawing Sheets

LASER CATHETER DELIVERY SYSTEM FOR CONTROLLED ATHEROMA ABLATION COMBINING LASER ANGIOPLASTY AND INTRA-ARTERIAL ULTRASONIC IMAGINING

BACKGROUND OF THE INVENTION

Atherosclerosis, in which a vessel gets partially or fully blocked by atheroma, is a common disease in the western world. Because of this there is a large research activity for developing catheter methods to remove the atheroma or expand the lumen of the artery. In laboratory experiments it has been possible to obtain ablation of the atheroma using laser light. This gives hopes for a method that can remove the atheroma even when there is only a thin hole left or full blocking of the artery.

A critical problem with this application is the dosage and direction of the laser light for accurate removal of the atheroma without damaging the arterial wall. This invention relates to an intravascular catheter for angioplasty using laser light for atheroma ablation and combining it with ultrasonic imaging of the atheroma for guidance of the laser light to obtain precise ablation without damaging the arterial wall. Ultrasonic Doppler blood velocity measurements may also be used to monitor the change in blood flow caused by the increased lumen. The invention also comprises a complete laser beam delivery system for intra-arterial laser angioplasty.

The laser light is delivered to the site using an optical fiber. At the tip of the catheter an ultrasonic transducer is located, and the basic idea of the invention is that the ultrasound transducer and the tip of the optical fiber are mounted so that the directions of the ultrasonic beam and the laser beam are related so that the ultrasound beam can be used to image the atheroma and the arterial wall, and the laser beam can be directed in any selected direction in the image, especially directions where an atheroma is indicated, for controlled ablation of the atheroma. This can be obtained by mounting the ultrasonic transducer and the fiber tip so that the two beam directions coincide, or with different directions of the two beams, the laser beam can be steered to a known direction in the image generated by the ultrasonic beam. Coincident directions of the beams can be obtained by (i) The fibre tip penetrates the ultrasound transducer with such a small hole that it has negligible effect on the ultrasound beam, and the hole is large enough to feed through the laser light, so that the direction of the laser light and the ultrasound beam substantially coincide. This is schematically illustrated in FIG. 1.

Figure 2:
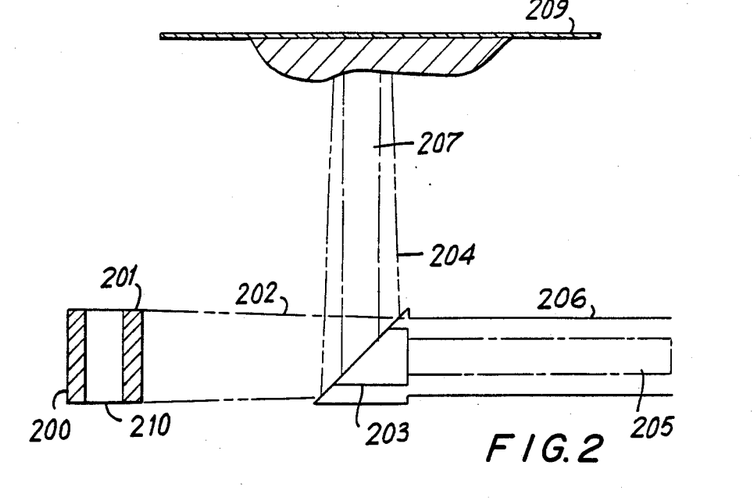
FIG. 2 schematically shows another embodiment of the tip of a catheter according to the invention where the ultrasound and laser beam directing means is composed of a mirror to reflect the ultrasound beam off at an angle, and a mirror and/or prism arrangement and-/or bending of the fiber tip for refracting the laser beam so that the two beams coincide after this.

(ii) The laser beam is bent off at an angle by a beam directing arrangement using either a mirror, prism arrangement, bending of the fiber tip, or combination of the three. The ultrasound transducer is mounted at a distance from this arrangement and radiating towards said arrangement which acts as a mirror for the ultrasound beam, so that the ultrasound beam is reflected into the same direction as the laser beam. A typical example of such an arrangement is schematically shown in FIG. 2.

Figure 3:
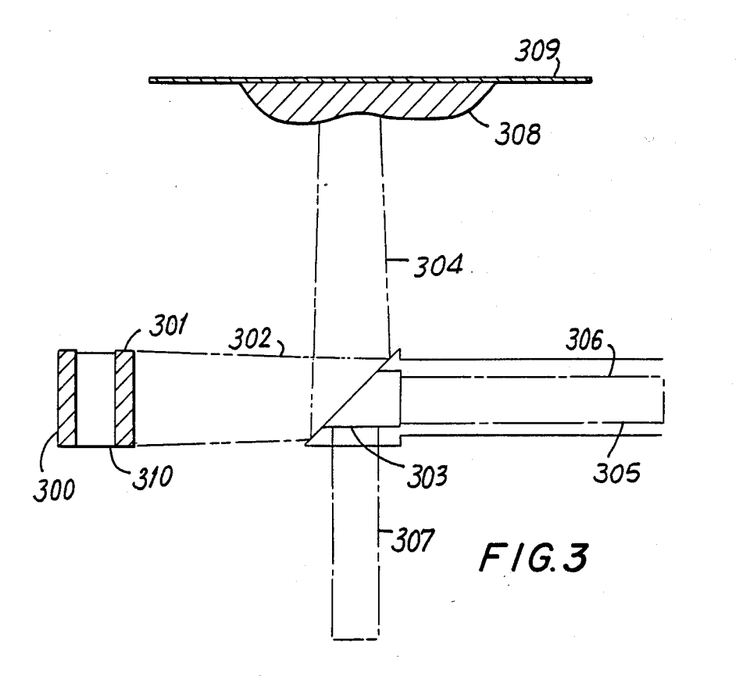
FIG. 3 schematically shows the tip of still another catheter according to the invention, where the ultrasound and laser beam directing means is composed of a mirror to reflect the ultrasound beam off at an angle and reflection of the laser beam in the opposite direction with the same arrangement so that a defined interrelation between the two beam directions is obtained.

An example of a method by which the beam directions are not coinciding, but interrelated so that the image obtained by the ultrasound beam can be used as a reference for guiding the laser beam, is schematically illustrated in FIG. 3. Here the laser beam is mirrored in the opposite direction to the ultrasound beam, and by rotating the mirror, the laser beam can be aligned to a previous, well known direction of the ultrasound beam.

Figure 5:
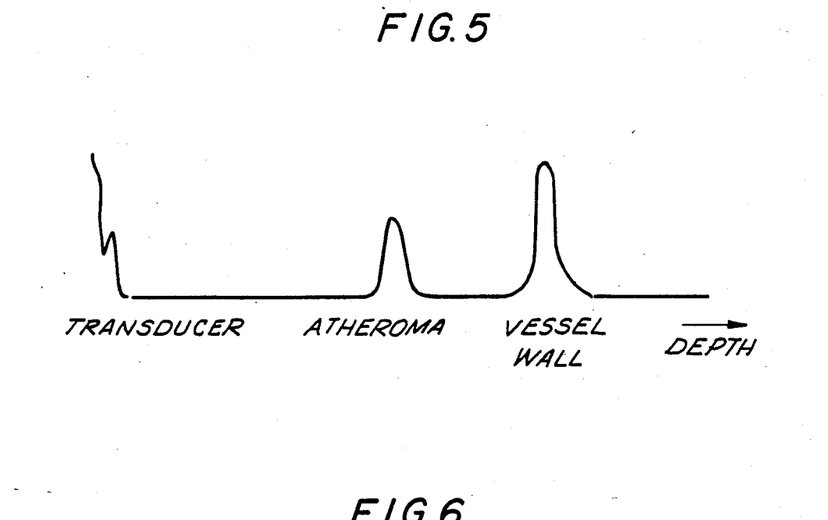
FIG. 5 shows an A-mode display of the atheroma and arterial wall from the reflections of an ultrasonic pulse.
Figure 6:
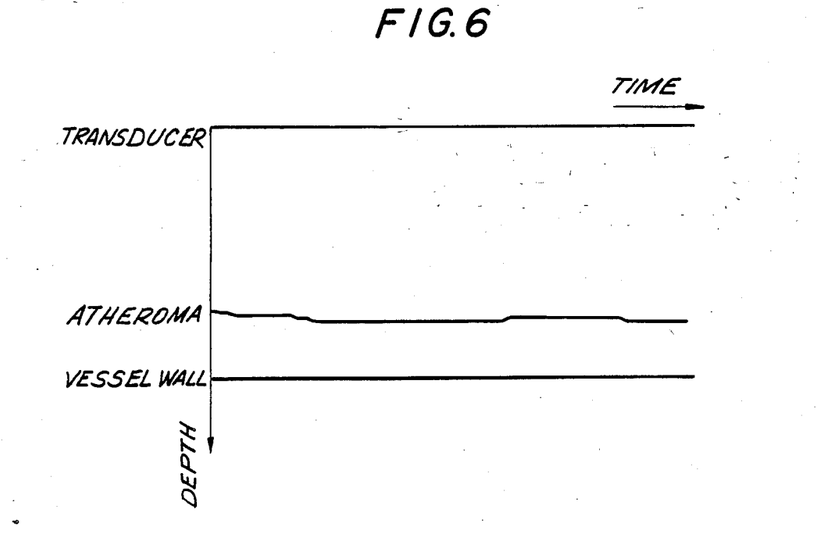
FIG. 6 shows a M-mode display of the atheroma and the arterial wall from the reflections of an ultrasonic pulse.

The ultrasound transducer can be used for pulse echo imaging in the following modes (i) A- or M-mode where range resolution is obtained visualizing the different structures of the atheroma and the arterial wall, as illustrated in FIG. 5 and FIG. 6 respectively.

Figure 7:
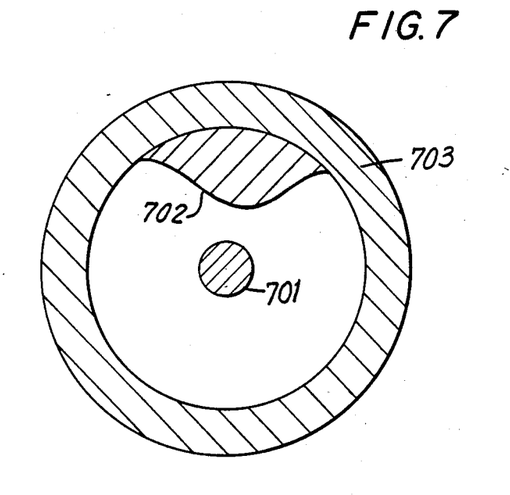
FIG. 7 shows a 2-dimensional cross sectional ultrasound image of a vessel with atheroma obtained by rotating the beam directing means of the catheter tip in FIGS. 2 and 3.

(ii) The beam direction can be scanned in a plane to generate a 2-dimensional cross section image of the atheroma and the artery, as illustrated in FIG. 7.

Figure 8:
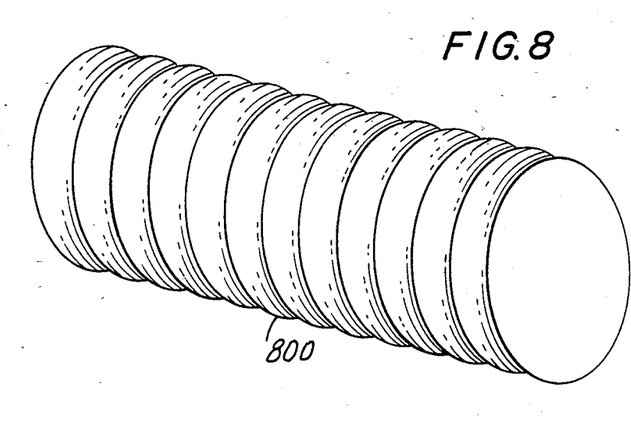
FIG. 8 indicates how a 3-dimensional display of the vessel and the atheroma can be obtained from 2-dimensional cross sections at defined positions longitudinally along the axis of an artery.

(iii) The 2-dimensional scan planes can be moved under position control by moving the catheter along the vessel to generate 3-dimensional images of the atheroma and the arterial wall, as illustrated in FIG. 8. This can be obtained by mounting a longitudinal position sensor, for instance using an optical grating, to the portion of the catheter which is outside the body. The third scan dimension is then obtained by pulling the catheter out of the artery, using the position indication to store 2-dimensional images at defined sections.

By imaging we thus mean any kind of presentation of the backscattered ultrasound which relates a portion of the signal to spatial location of the scatterers in the region being sonified. By direction the laser beam along the ultrasonic beam we can obtain a precise observation of both the location of the atheroma to decide where to apply laser light, and continuous monitoring of the effect of the laser light on the atheroma to adaptively determine the energy levels to be applied and when to stop the illumination to avoid damage to the arterial wall. By high energies of the laser light, the ultrasound imaging might be affected by the gas or debris from the ablation of the atheroma, so that it can be advantageous to apply imaging and laser treatment in a time sequence using a spatial interrelation between the beams, so that the laser beam can be directed in a defined direction where an ultrasound image has been obtained. To obtain this, the beam directions do not need to coincide, but they need to be interrelated so that the laser beam can be directed towards a defined part of a previously generated ultrasound image, and the ultrasound beam can be directed towards the place where laser irradiation has occurred, to monitor the effect of the irradiation.

In its broader aspect, the intra-arterial laser angioplasty delivery system according to the invention comprises:

a combined laser and ultrasound catheter comprised of
  means for emitting a laser beam in an artery towards an atheroma for ablation of the atheroma,
  optical fiber means for feeding laser light from a laser to said emitting means,
  an ultrasound transducer for intra-arterial imaging of tissue structures like the atheroma, the vessel wall and surrounding tissue, by emitting a pulsed ultrasound beam towards said tissue structures and also arranged to receive backscattered ultrasound from said tissue structures, and
  beam directing means arranged to direct the ultrasound beam towards said tissue structures and also arranged so that the laser beam can be brought into for practical purposes any of the directions the ultrasound beam can assume for imaging, so that the laser beam can be steered towards a portion of the ultrasound image indicating a portion of an atheroma for ablation of said portion of the atheroma, receive circuits adapted to receive and process the backscattered ultrasound for imaging of the tissue structures, and means for analysing said ultrasound image, either manually or automatically, to determine the presence of atheroma so that said image can be used to direct the laser beam towards the regions in the ultrasound image which have been determined to represent atheroma and determine the intensity and the dosage of the laser beam for accurate ablation of said atheroma.

Another aspect of this invention relates to an intra-arterial laser angioplasty catheter comprising:

means for emitting a laser beam in an artery towards an atheroma for ablation of the atheroma, optical fiber means for feeding laser light from a laser to said emitting means, an ultrasound transducer for intra-arterial imaging of tissue structures like the atheroma, the vessel wall and surrounding tissue, by emitting a pulsed ultrasound beam towards said tissue structures and also arranged to receive backscattered ultrasound from said tissue structures, and beam directing means arranged to direct the ultrasound beam towards said tissue structures and also arranged so that the laser beam can be brought into substantially any of the directions the ultrasound beam can assume for imaging, so that the laser beam can be steered towards a portion of the ultrasound image indicating a portion of an atheroma to hit said portion of the atheroma, so that the ultrasound image can be used to guide the laser ablation of the atheroma.

DETAILED DESCRIPTION OF THE INVENTION

FIGS. 1, 2, and 3 are schematic schetches of basic ideas of the invention, namely how a pulsed ultrasound beam can be used to obtain information of how to steer laser irradiation for ablation of the atheroma. The drawings are schematic, illustrating basic principles, and in practical implementations different variations can be used such as sending the beams forward in a cone instead of at right angles. The arrangement will be suitably mounted in a fully or partially closed catheter with transluminant windows for the ultrasound and laser beams, so that any part of the tissue is kept away from contact with the moving parts of the beam directing system. For simplicity the cover of the catheter is not shown since it is not part of the essentials of the invention.

Figure 1A:
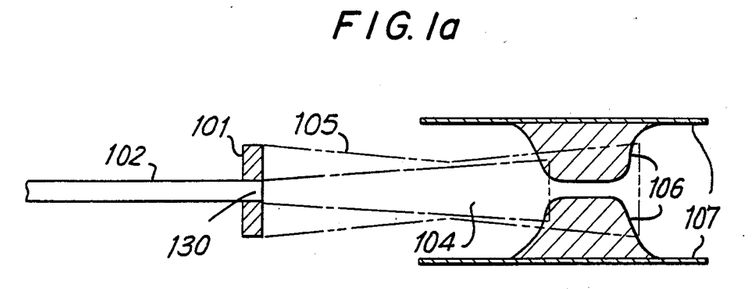
FIGS. 1a and b both schematically show the tip of a catheter according to the invention where the optical fiber tip penetrates the ultrasound transducer so that the ultrasound beam direction and the laser beam direction substantially coincide.
Figure 1B:
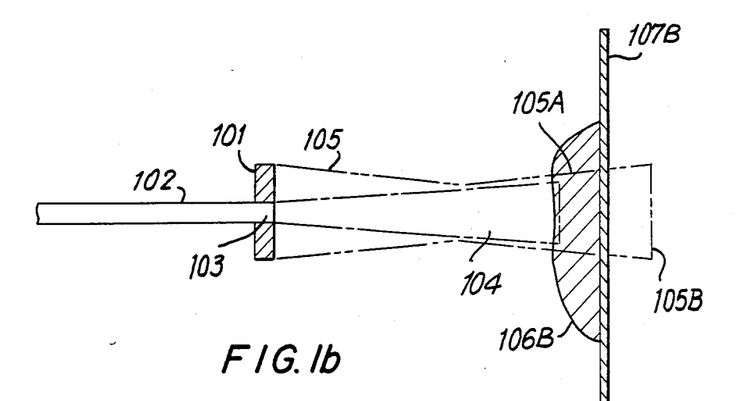

FIGS. 1a and b both show a schematic illustration of an ultrasonic transducer element 101 mounted at the tip of a catheter emitting an ultrasonic beam 105 in the front of the catheter tip. A laser beam is guided through an optical fiber, 102, which passes through a hole, 103, in the ultrasound transducer element so that a laser beam, 104, is emitted along the same direction as the ultrasound beam. In FIG. 1a the two beams point axially along the artery, hitting an atheroma 106 which partially blocks the artery defined by the arterial wall 107. In FIG. 1b the tip of the catheter is bent so that the two beams point in the radial direction of the artery hitting an atheroma 106b which is seated on the arterial wall 107b.

The ultrasonic beam is pulsed to obtain range resolution to resolve the distance to the surface of the atheroma and the arterial wall. In a typical application the two beams will hit atheroma, 106. The ultrasonic beam will be partially reflected, but some of the energy will traverse into the tissue and be partially reflected from within the tissue and tissue interfaces to give an image of structures inside the atheroma for determination of the calcification or imaging of the arterial wall. Like in FIG. 1b some of the energy 105A will traverse the atheroma and hit the arterial wall 107B and be partially reflected and part of this energy, 105B, will be transmitted further into the tissue. The laser beam, 104, will, with a proper selection of the wavelength of the laser light, be absorbed at the surface of the atheroma 106B so that ablation of the atheroma is obtained. Since the laser beam coincides with the ultrasound beam direction, the ultrasound image will give an instantaneous depiction of the effect of the laser light, which can be used as a control of the laser irradiation.

Using a well known A-mode display of the backscattered ultrasound from a short transmitted pulse, the atheroma and the arterial or vessel wall can be depicted as schematically shown in FIG. 5. This can be used to align the laser beam against the atheroma, observe the effect of the irradiation, and make sure that damaging of the arterial wall is avoided. The well known M-mode display of the ultrasound echos can also be used, as shown in FIG. 6. This gives a better indication of the temporal effect of the laser irradiation.

In the configuration of FIG. 1a the ultrasound transducer can also be used for ultrasonic Doppler measurements of the blood velocity in the artery by which we can monitor the haemodynamic effect of the ablation.

FIGS. 2 and 3 illustrate embodiments where mirrors are used to direct the ultrasound beam. In FIG. 2 a beam directing means, composed of for instance a mirror and/or prism arrangement, is used to direct the laser beam in the same direction as the ultrasound beam, and in FIG. 3 the laser beam is mirrored in the opposite direction of the ultrasound beam.

In FIG. 2 an ultrasonic transducer, 201, is illustrated, emitting an ultrasonic beam 202. This beam is reflected by the arrangement 203 which acts as an ultrasonic mirror, and the beam is bent off at a direction 204. A laser beam is guided through an optical fiber, 205, and is bent off at the beam directing arrangement 203 so that the laser beam direction, 207, after this bending coincides with that of the ultrasonic beam, 204.

In a typical application the two beams will be used simultaneously and hit the atheroma 208. An arterial wall 209 is also shown. In the same way as in FIG. 1 an A-mode and M-mode ultrasound image can be generated and used for guidance of the laser irradiation. By rotating the beam directing assembly 206, the two beams can be scanned in a plane transverse to the catheter direction. The ultrasound can then be used to form a 2-dimensional image of the atheroma and the arterial wall as illustrated in FIG. 7, in which 701 illustrates a cross section of the catheter arrangement, 702 illustrates the image of the atheroma, 208, and 703 illustrates the image of the arterial wall, 209. This 2-dimensional image is then used to find atheroma and for control of the laser beam intensity and pulsing so that atheroma portions of the image are irradiated by laser light.

Since the two beams are used simultaneously with the same direction, the ultrasound image will be an instantaneous guide for controlling the intensity and pulsing of the laser beam, and will also give an instantaneous monitoring of the effect of the laser irradiation. By high energy levels of the laser light, debris from the ablation can disturb the ultrasound imaging. It can then be advantageous to not shoot the laser light along the same direction at the same time as the ultrasound beam, to avoid the disturbance in the image.

This can be done in several ways:

(i) With stationary direction of the ultrasound beam and A- or M-mode imaging, the ultrasound beam and the laser beam can be activated separately in a time sequence.

(ii) With scanning of the ultrasound beam for 2-dimensional imaging a similar time sequence can be used by first doing an ultrasound scan to generate an image, and then moving the beam directing means so that the laser is pointed towards a selected portion of the ultrasound image for irradiating atheroma for a selected portion of the time, and then doing another ultrasound scan to monitor the effect of the laser irradiation.

(iii) The beam directing means can point the ultrasound and laser beams in different directions in a plane and the beams are scanned and active simultaneously but at different directions in the plane. The direction of the laser beam within the ultrasound image is known at any time, so that the image can be used for guiding the intensity and pulsing of the laser beam, and the ultrasound beam will shortly afterwards sweep over areas that have been irradiated by the laser light to monitor the effect of the laser irradiation.

An arrangement which gives an implementation of the last method is shown in FIG. 3. In this figure an ultrasonic transducer, 301, is illustrated, emitting an ultrasonic beam 302. This beam is reflected by the arrangement 303 which acts as an ultrasonic mirror, and the beam is bent off at a direction 304. A laser beam is guided through the optical fiber, 305, and is reflected at an angle by the mirror 303 so that the laser beam direction, 307, after this reflection is opposite to that of the ultrasonic beam. An atheroma 308 and an arterial wall 309 are also shown. In a typical application the assembly 306 is rotated to generate a cross sectional ultrasound image of the artery like in FIG. 7. In the image the laser beam will then at any instant be in the opposite direction of the ultrasound beam.

In FIG. 2 and FIG. 3 a second ultrasound transducer 200, respectively 300, is mounted to the same, acoustically isolating holder 210, respectively 310, as the first transducer 201, respectively 301. This transducer radiates in the oposite direction of the former, and will thus give a beam along the artery which can be used for ultrasound Doppler measurements to monitor the blood velocity downstream from the obstruction for assessment of the hemodynamic effect of the ablation.

By moving the catheter along the vessel, two-dimensional images of the artery can be obtained at defined cross sections. This can for example be done by mounting a longitudinal position sensor on the catheter outside the body and pulling the catheter out under position control. Cross sectional images are then stored for defined positions, and these images can then be used for three-dimensional reconstruction of the vessel and the atheroma in a manner known per se, and as illustrated in FIG. 8, where one of the cross sections is indicated at 800.

Figure 9:
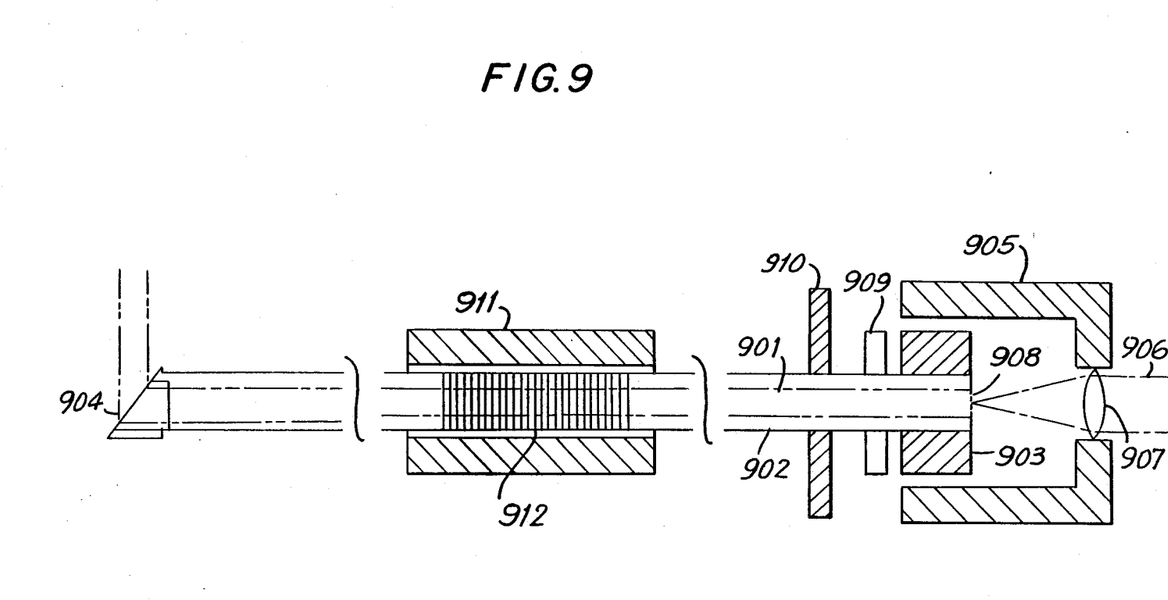
FIG. 9 shows an example of a system for rotating the beam directing assembly manually or by a motor, together with a lens for coupling of the laser light into the optical fiber. A longitudinal position sensor for measuring longitudinal changes in the position of the catheter tip for 3-dimensional imaging of the vessel and the atheroma is also indicated.

An example of a system for rotational steering of the beam directing system together with a third dimension position sensing is shown in FIG. 9. The optical fiber 901 is enclosed in a bendable steel tubing 902 which connects the rotor 903 of the motor and the beam directing means 904. As described earlier the rotating assembly will be covered by the catheter tube to avoid contact between the moving parts in the catheter and the tissue. This cover is for the sake of simplicity not shown in the figure. The stator 905 of the motor is mounted to a suspension (not shown) which is fixed relative to the incoming laser beam 906 which shines through a lens 907 in the housing so that the beam is focussed onto the optical fiber tip 908. A rotary position sensor 909 is connected to the steel tubing to provide the rotary position of the beam directing system. Because of the length of the steel tube there can be error in the monitoring of the angular position of the beam directing arrangement caused by twisting of the steel tube. This error can be reduced by mounting a position sensor close to the beam directing system at the far end tip of the catheter.

The motor and the position sensor can be used in a servo loop for precise positioning of the beam directing means 904. The beam directing system can also be rotated manually by for instance turning the wheel 910. An optical position sensor 911 which reads gratings 912 in the catheter to determine changes in the longitudinal position of the catheter is schematically indicated in the figure. The position sensor is mounted outside the patient body, and the catheter tip 904 can be moved longitudinally within the artery by pulling the catheter in and out. Two-dimensional cross sectional images at different longitudinal positions can then be stored and used for reconstructing a three-dimensional image of the atheroma and artery. In the figure the catheter is indicated to be straight, but generally bends of the catheter must exist. For instance when moving the catheter in and out of the artery through the longitudinal position sensor, we could move the motor assembly, but with a U-bend of the catheter between the position sensor and the motor a limited pulling of the catheter out of the artery can be obtained without moving the motor assembly.

Figure 4:
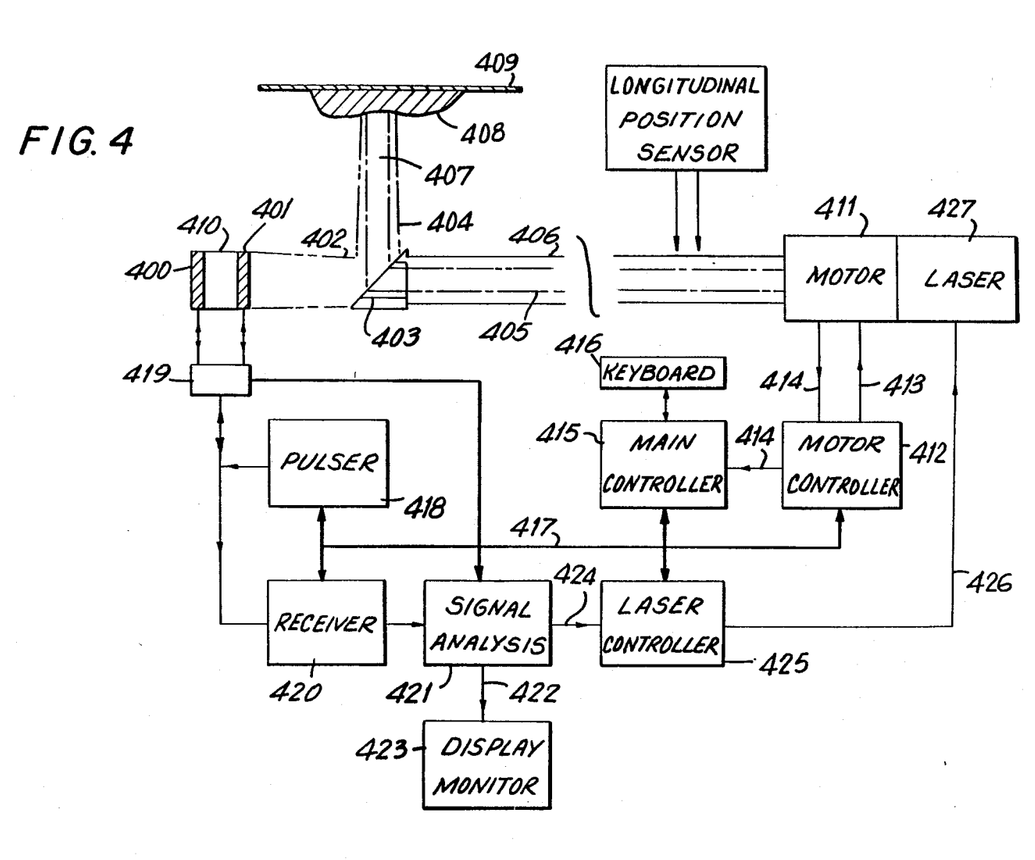
FIG. 4 shows a complete block diagram of a combined ultrasound imaging and laser light delivery system.

An arrangement of necessary functional blocks or electronic equipment units for obtaining a more complete delivery system for intra-arterial laser angioplasty, is also shown in connection with the catheter in FIG. 4. The system is set up and controlled through the main controller unit 415, which can be set up by an operator through a keyboard 416. The main controller sets up the rest of the system through a controller bus 417 which is composed of multibit address and data signals together with necessary analog control signals. The bus is assumed to be bidirectional so that information can flow both from the main controller to the subunits as well as from the subunits to the main controller.

In the figure a motor 411 is used to move the beam directing system 403. The motor is driven by the motor controller 412 which feeds a drive signal 413 to the motor. The signal 414 indicates the position of the beam directing system and is fed back to the motor controller so that the beam directions can be steered by a servo-like method. For precise adjustment of the beam directions manual adjustment can also be used either by direct manual movement of the mechanical linkage to the beam directing system or via the servo system using the motor as a drive.

The laser is shown as a block 427 attached to the motor. The reason for this is that the optical coupling into the fiber and the drive link between the motor and the beam directing system is an integral design. In a typical situation the laser light is fed from the laser cavity resonator to the fiber coupling, either through a lens and mirror/prism system or through a fiber. The light is then focused onto the catheter fiber end by a mechanical design in conjunction with the linkage between the motor and the fiber system so that the light enters the fiber even when the beam directing system is moving. An example of such a coupling has allready been described in relation to FIG. 9.

In imaging mode the transducer 401 is connected to the pulser 418 and the receiver 420 via the select switch 419 which is set up by the main controller 415 via the control bus. The beam direction position signal 414 is also fed back to the main controller 415. Depending on the position of the beam directing system and the mode selection of the system, the main controller triggers pulses via the pulser 418 which is converted to an ultrasound pulse by the transducer 401. These pulses are deflected into the direction 404 by the beam directing system 403 which acts as an ultrasonic mirror. The pulses are reflected by the atheroma 408, partially transmitted into the atheroma and reflected by inhomogeneities in the atheroma and the arterial wall 409. The reflected signal is also mirrored by 403 and is picked up by the same transducer and converted to an electrical signal which is amplified by the receiver 420, and undergoes further processing by the signal analyzer block 421. This block also generates display signals 422 which are fed to a display monitor 423.

A typical signal analysis to be done in block 421 is compression and envelope detection of the received signal which is standard for ultrasound imaging systems. In a two dimensional imaging mode described in relation to FIGS. 2 and 3, a typical display on the screen would be as shown in FIG. 7, while for stationary positions of the beam directing system, an A- or M-mode display as shown in FIGS. 5 and 6 could be used.

The signal is then further analysed to determine whether the ultrasonic beam is intersecting atheroma or which portion of the image is atheroma. This can be done manually by pattern recognition from observing the image on the screen and then using a cursor to outline the atheroma region, or automatically through tissue characterisation based on for instance relative appearance of the signal intensity in the image. The backscattered signal intensity will increase from any presence of calcification in the atheroma, so that the intensity can be used to differentiate calcified atheroma from the normal tissue. Geometrical deviation of the arterial cross section from the normal circular shape can also be used to distinguish atheroma from normal tissue.

Having thus, based on the backscattered ultrasound, differentiated between atheroma and normal tissue, either manually or automatically, a signal 424 is fed to the laser controller 425 which, linked to the direction of the laser beam relative to what have been determined to represent atheroma in the image, determines the laser irradiation of the atheroma both by pulse rate and pulse intensity through a signal 426 to the laser 427, for precise ablation of the atheroma.

For Doppler measurements the transducer 400 is by the selector 419 connected to the pulser 418 and receiver 420. The signal analysis is then a standard Doppler signal analysis for determining the blood velocities in front of the catheter. These velocity tracings are then displayed on the display monitor 423. The blood velocity measurements can be combined in a well known way with the imaging of the arterial cross section to determine volume flow of blood.

We claim:

1. An intra-arterial laser angioplasty catheter, comprising:
    an elongated catheter tube for intra-arterial insertion and extension to an angioplasty site and having a distal end for operative disposition proximate the angioplasty site;
    optical fiber means extending along and within said tube for transmitting laser irradiation to the distal end of the catheter tube for selective tissue ablation;
    ultrasound transducer means proximate the distal end of said tube for emitting a pulsed ultrasound beam toward tissue at the angioplasty site and for receiving ultrasound reflections of said emitted beam to thereby provide intra-arterial imaging of tissue structures;
    means proximate the distal end of said tube for directing said laser irradiation from the catheter in a first direction and for directing said emitted ultrasound beam from the catheter in a second direction, said first and second directions having a fixed angular relation therebetween; and means operable for rotating said directing means relative to said catheter tube so as to concurrently selectively vary said first and second directions while maintaining said fixed angular relation therebetween and thereby selectively steer said emitted ultrasound beam and laser irradiation toward tissue structures for imaging and ablation, respectively, thereof, whereby said intra-arterial imaging enables steering of said laser irradiation by selective rotation of said directing means to guidedly direct the laser irradiation for intra-arterial tissue ablation in accordance with the imaging provided by said ultrasound beam.

2. An intra-arterial laser angioplasty catheter in accordance with claim 1, wherein said first and second directions of said laser irradiation and said emitted ultrasound beam are coincident.

3. An intra-arterial laser angioplasty catheter in accordance with claim 27, wherein said first and second directions of said laser irradiation and said emitted ultrasound beam define a fixed angular relation therebetween of approximately 180°.

4. An intra-arterial laser angioplasty catheter in accordance with claim 1, wherein said means for rotating said directing means is operable for selectively varying said first and second directions of the laser irradiation and the emitted ultrasound beam about an axis substantially parallel to an elongated direction of said catheter tube proximate the distal end thereof.

5. An intra-arterial laser angioplasty catheter in accordance with claim 1, wherein said first and second directions of the laser irradiation and the emitted ultrasound beam lie substantially perpendicular to an elongate direction of said catheter tube proximate the distal end thereof.

6. An intra-arterial laser angioplasty catheter in accordance with claim 1, wherein proximate the distal end of the catheter tube, said ultrasound transducer means emits the ultrasound beam and said optical fiber emits the laser irradiation each toward the other.

7. An intra-arterial laser angioplasty catheter in accordance with claim 6, wherein said directing means is disposed between said ultrasound transducer means and the laser irradiation emissions from said optical fiber so that the ultrasound beam and laser irradiation are both directed toward said directing means.

8. An intra-arterial laser angioplasty catheter in accordance with claim 1, wherein said directing means comprises a mirror means for deflecting at least said emitted ultrasound beam and thereby directing the ultrasound beam in said second direction.

9. An intra-arterial laser angioplasty catheter in accordance with claim 8, wherein said directing means comprises a mirror means for deflecting at least said laser irradiation from said optical fiber means and thereby directing the laser irradiation in said first direction.

10. An intra-arterial laser angioplasty catheter in accordance with claim 1, further comprising means for sensing the amount of longitudinal intra-arterial extension of the catheter tube distal end.

11. An intra-arterial laser angioplasty catheter in accordance with claim 1, wherein said catheter tube is intra-arterially insertable and extendable along a third direction, and said ultrasound transducer means includes means for emitting a second ultrasound beam in said third direction and for receiving reflected ultrasound reflections of said second beam.

12. An intra-arterial laser angioplasty catheter in accordance with claim 11, wherein said third direction is oriented longitudinally along an artery in which said catheter tube is inserted.

* * * * *